United States Patent
Mitschke et al.

(10) Patent No.: US 6,851,855 B2
(45) Date of Patent: Feb. 8, 2005

(54) REGISTRATION METHOD FOR NAVIGATION-GUIDED MEDICAL INTERVENTIONS

(75) Inventors: Matthias Mitschke, Nuremberg (DE); Dieter Ritter, Fuerth (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/410,716

(22) Filed: Apr. 10, 2003

(65) Prior Publication Data
US 2004/0013240 A1 Jan. 22, 2004

(30) Foreign Application Priority Data
Apr. 10, 2002 (DE) .......................... 102 15 808

(51) Int. Cl.⁷ .............................. G01D 18/00
(52) U.S. Cl. ........................ 378/207; 378/205
(58) Field of Search .................. 378/20, 162–164, 378/204–207

(56) References Cited

U.S. PATENT DOCUMENTS

| | | | |
|---|---|---|---|
| 4,991,579 A | 2/1991 | Allen | 600/426 |
| 5,442,674 A | 8/1995 | Picard et al. | 378/20 |
| 5,951,475 A | 9/1999 | Gueziec et al. | 600/425 |
| 6,050,724 A | 4/2000 | Schmitz et al. | 378/205 |
| 6,317,621 B1 | 11/2001 | Graumann et al. | 600/424 |
| 6,493,574 B1 * | 12/2002 | Ehnholm et al. | 600/429 |
| 2002/0018588 A1 | 2/2002 | Kusch | |
| 2002/0123680 A1 | 9/2002 | Vaillant et al. | |
| 2002/0172328 A1 * | 11/2002 | Dekel | 378/205 |
| 2004/0077942 A1 * | 4/2004 | Hall et al. | 600/428 |

FOREIGN PATENT DOCUMENTS

| | | |
|---|---|---|
| DE | OS 199 36 409 | 3/2001 |
| EP | 1 192 913 | 4/2002 |
| WO | WO 00/41626 | 7/2000 |

OTHER PUBLICATIONS

"Optimal Configuration for Dynamic Calibration of Projection Geometry of X–Ray C–arm Systems," Mitschke et al., IEEE 2000.

* cited by examiner

Primary Examiner—Edward J. Glick
Assistant Examiner—Jurie Yun
(74) Attorney, Agent, or Firm—Schiff Hardin LLP

(57) ABSTRACT

In a registration method for navigation-guided medical interventions using a position acquisition system, an X-ray device and an X-ray calibration phantom having X-ray-positive marks, the coordinates of marks of the X-ray calibration phantom that are present in the measurement volume of the X-ray device and imaged in the reconstructed volume are determined in a coordinate system allocated to the measurement volume of the X-ray device) and in a coordinate system allocated to the position acquisition system. The coordinate transformation between the coordinate system allocated to the measurement volume and the coordinate system allocated to the position acquisition system is determined on the basis of the coordinates of the X-ray-positive marks in the coordinate system allocated to the measurement volume and on the basis of the coordinates of the X-ray-positive marks in the coordinate system allocated to the position acquisition system.

11 Claims, 3 Drawing Sheets

REGISTRATION METHOD FOR NAVIGATION-GUIDED MEDICAL INTERVENTIONS

BACKGROUND OF THE INVENTION

1. Field of the Invention

The invention is directed to a registration method for navigation-guided medical interventions, of the type wherein a coordinate transformation between a coordinate system of a position acquisition system and a coordinate system of a measurement volume of a X-ray device is determined, and is employed for the navigation.

2. Description of the Prior Art

Navigation is being increasingly used for supporting medical interventions, meaning that the guidance of a medical instrument relative to a patient or relative to a tissue region of the patient undergoing treatment that is supported by means of optical image information. In image of the instrument is mixed into a 2D or 3D image of the patient acquired with an X-ray device. In this way, an operator can guide an instrument that has at least partly penetrated into the patient and whose tip, for example, is no longer directly visible due to the penetration into body tissue. This instrument is guided relative to the tissue region under treatment on the basis of the image information without running the risk of unintentionally injuring the patient.

In order to enable such a navigation-guided intervention, i.e. in order to be able to mix an image of the instrument into image information of a patient with an accurate position and orientation, it is necessary to produce a mathematical relationship in the form of a coordinate transformation between a coordinate system of the image information of the patient, or a coordinate system of the reconstructed volume of the patient, and a coordinate system with reference to which the positions of the instrument to be navigated are indicated. To this end, artificial marks sometimes are arranged at the patient or anatomical marks are defined, for example prominent bone structures. The anatomical or artificial marks must be clearly visible in the image information of the patient acquired with the X-ray device and must be easily reachable at the patient. The artificial marks are secured, for example, to the skin surface of the patient in order to undertake a registration, which is understood to mean the determination of the spatial transformation rule between the coordinate system in which the positions of the instrument to be navigated are defined and the coordinate system of the image information or of the reconstructed volume, of the patient. The marks usually must be approached with the instrument individually and in the correct sequence in order to be able to determine the coordinate transformation between the two coordinate systems. In the case of extremely precise medical interventions, the marks are rigidly secured to the body of the life form. Examples are the attachment of a stereotactic frame to the head of a patient or the attachment of marks in bones or at the spinal column of a patient. The attachment of the marks may ensue in a separate operation, since the marks must already be attached before a preoperative imaging that is frequently employed for the navigation.

The attachment and registration of the marks, accordingly, is a relatively unpleasant procedure for a patient and also is relatively time-consuming for an operator in preparation for a navigation-guided intervention.

SUMMARY OF THE INVENTION

An object of the present invention is to provide a simplified method for determining the transformation rule.

This object is achieved in a method according to the invention wherein a series of 2D projections of an X-ray calibration phantom that is aligned relative to the X-ray device and has X-ray-positive marks, is acquired with an X-ray device, and a volume dataset is reconstructed; from the acquired 2D projections of the X-ray calibration phantom. The coordinates in a coordinate system allocated to the measurement volume of the X-ray device and the coordinates in a coordinate system allocated to a position acquisition system are obtained from the X-ray-positive marks of the X-ray calibration phantom imaged in the reconstructed volume, the marks being situated in a measurement volume of the X-ray device. The coordinates in the coordinate system allocated to the measurement volume of the X-ray device and the coordinates in the coordinate system allocated to the position acquisition system are thus available for a number of X-ray-positive marks of the X-ray calibration phantom, so that the coordinate transformation between the coordinate system allocated to the measurement volume and the coordinate system allocated to the position acquisition system can be determined from these point pairs. Accordingly, coordinates of a medical instrument acquired with respect to the coordinate system of the measurement volume for medical applications, for example, can be transformed into coordinates of the coordinate system of the measurement volume, so that it is possible to mix images of the instrument into images of a subject generated with the X-ray device without marker-dependent registration, i.e. without markers to be attached to a subject under treatment.

According to one version of the invention, a selection is made of X-ray-positive marks of the X-ray calibration phantom that are present in the measurement volume of the X-ray device and that are imaged in the reconstructed volume, the coordinates of these marks being automatically determined in the coordinate system allocated to the measurement volume. A specific sequence of the marks usually is defined by the, selection of the X-ray-positive marks, which facilitates the formation of point pairs for determining the coordinate transformation. The coordinates of the centers of gravity of the marks preferably are identified in the automatic determination of the coordinates of the X-ray-positive marks in the coordinate system allocated to the measurement volume.

In another version of the invention, the geometry of the X-ray calibration phantom and the coordinates of the X-ray-positive marks of the X-ray calibration phantom in a coordinate system allocated to the X-ray calibration phantom are known. After the reconstruction of the volume of the X-ray calibration phantom, the orientation of the X-ray calibration phantom in the coordinate system allocated to the measurement volume is determined in a first step, for example by determining the orientation of the edges of the X-ray calibration phantom by means of 3D edge extraction. In a second step, the coordinates of X-ray-positive marks of the X-ray calibration phantom that are present in the measurement volume and imaged in the volume are determined in the coordinate system allocated to the measurement volume based on the identified orientation of the edges of the X-ray calibration phantom in the coordinate system allocated to the measurement volume and based on the known coordinates of the marks in the coordinate system allocated to the X-ray calibration phantom. In this way as well, accordingly, the coordinates of the X-ray positive marks can be determined in the coordinate system allocated to the measurement volume of the X-ray device for the formation of the point pairs.

In an embodiment of the invention, the coordinates of the X-ray-positive marks of the X-ray calibration phantom that are present in the measurement volume and imaged in the volume are determined with a pointer in the coordinate system allocated to the position acquisition system. The determination ensues such that the individual X-ray-positive marks selected for the determination of the transformation rule are tapped with the pointer that is detectable by a position acquisition system, for example with a tip of the pointer. Since the pointer is constructed in a defined way such that the coordinates of the tip of the pointer can be determined by the position acquisition system in the coordinate system of the position acquisition system, the coordinates of the tapped X-ray-positive marks can, accordingly, be determined in the position acquisition system.

In another version of the invention, the X-ray-positive marks are fashioned so that they also can be directly acquired by the position acquisition system. According to one embodiment of the invention, the position acquisition system is an optical position acquisition system and the marks are a matter of retro-reflection marks. In another version of the invention, the determination of the coordinates of the marks of the X-ray calibration phantom directly in the coordinate system of the position acquisition system can be automatically carried out by the position acquisition system.

In a further embodiment of the invention, markers that can be detected by the position acquisition system are arranged at the X-ray device, preferably in the form of a marker plate. A coordinate transformation between a coordinate system allocated to the markers arranged at the X-ray device and the coordinate system allocated to the measurement volume is determined on the basis of the markers arranged at the X-ray device. As a result of this coordinate transformation, a transformation rule between the coordinate system of the measurement volume and the coordinate system of the position acquisition system can be produced again after an adjustment of the X-ray device and the position acquisition system relative to one another. After such an adjustment the original coordinate transformation between the coordinate system allocated to the measurement volume and the coordinate system allocated to the measurement volume that is determined as described above is no longer valid.

In another version of the invention the X-ray device is a C-arm X-ray device the C-arm of which has an isocenter and is isocentrically adjustable. The origin of the coordinate system of the measurement volume preferably is in the isocenter of the C-arm. As a result thereof, the transformation rule between the coordinate system of the measurement volume and a coordinate system of the reconstructed volume can be determined in a simple way based on a reconstruction of a volume of an X-ray calibration phantom comprising X-ray-positive marks and can be employed for the navigation. This transformation rule usually is determined in a separate calibration event for the X-ray device wherein the projection matrices of the X-ray device are determined for the imaging.

DESCRIPTION OF THE PREFERRED EMBODIMENTS

Figure 1:
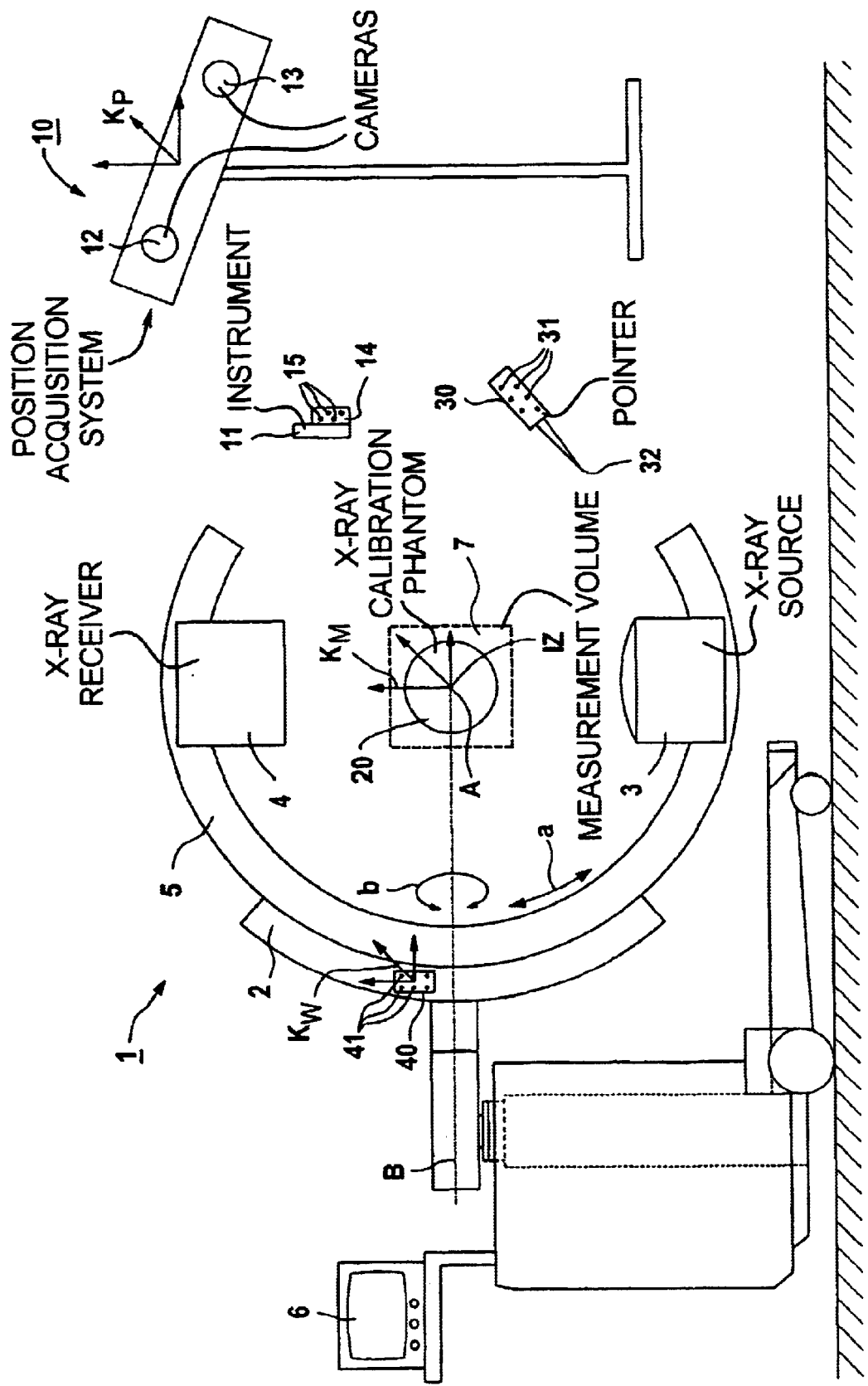
FIG. 1 is a schematic illustration of a medical interventional apparatus operable in accordance with a first embodiment of the inventive method.

The well-known C-arm X-ray device 1 shown in FIG. 1 has a support 2 at which a C-arm 5 provided with an X-ray source 3 and an X-ray receiver 4 is seated. The C-arm 5 in the present exemplary embodiment is isocentrically adjustable (see double arrow 'a') along its circumference around its isocenter IZ and its orbital axis A. Together with the support 2, the C-arm 5 is also isocentrically pivotable around its angulation axis B in the directions of the double arrow 'b'.

2D and 3D images of subjects, for example patients, can be acquired with the C-arm X-ray device 1 and can be presented on a display device 6. The devices required for this purpose, particularly an image computer, are implemented in a known way and are therefore not shown in FIG. 1 and need not be explicitly described.

Particularly for medical applications, navigation-guided interventions at a patient (not shown) are implementable with the C-arm X-ray device 1. For this reason, it is necessary to determine a coordinate transformation between a coordinate system $K_M$ allocated to a cuboid measurement volume 7 (schematically indicated in FIG. 1) of the C-arm X-ray device 1 this coordinate system has its origin in the isocenter IZ of the C-arm X-ray device 1 in the exemplary embodiment) and a coordinate system $K_P$ allocated to a position acquisition system 10 (schematically shown in FIG. 1) in which the coordinates of an instrument 11 to be navigated relative to a patient are also recited.

A position acquisition system 10 is used in the present exemplary embodiment that is a well-known optical position acquisition system having two cameras 12 and 13. Subjects provided with optical markers detectable by the cameras 12, 13 can be acquired with the cameras 12, 13, and their positions and orientations, i.e. their coordinates in the coordinate system $K_P$ allocated to the position acquisition system 10, can be determined by evaluating the camera images.

Figure 2:
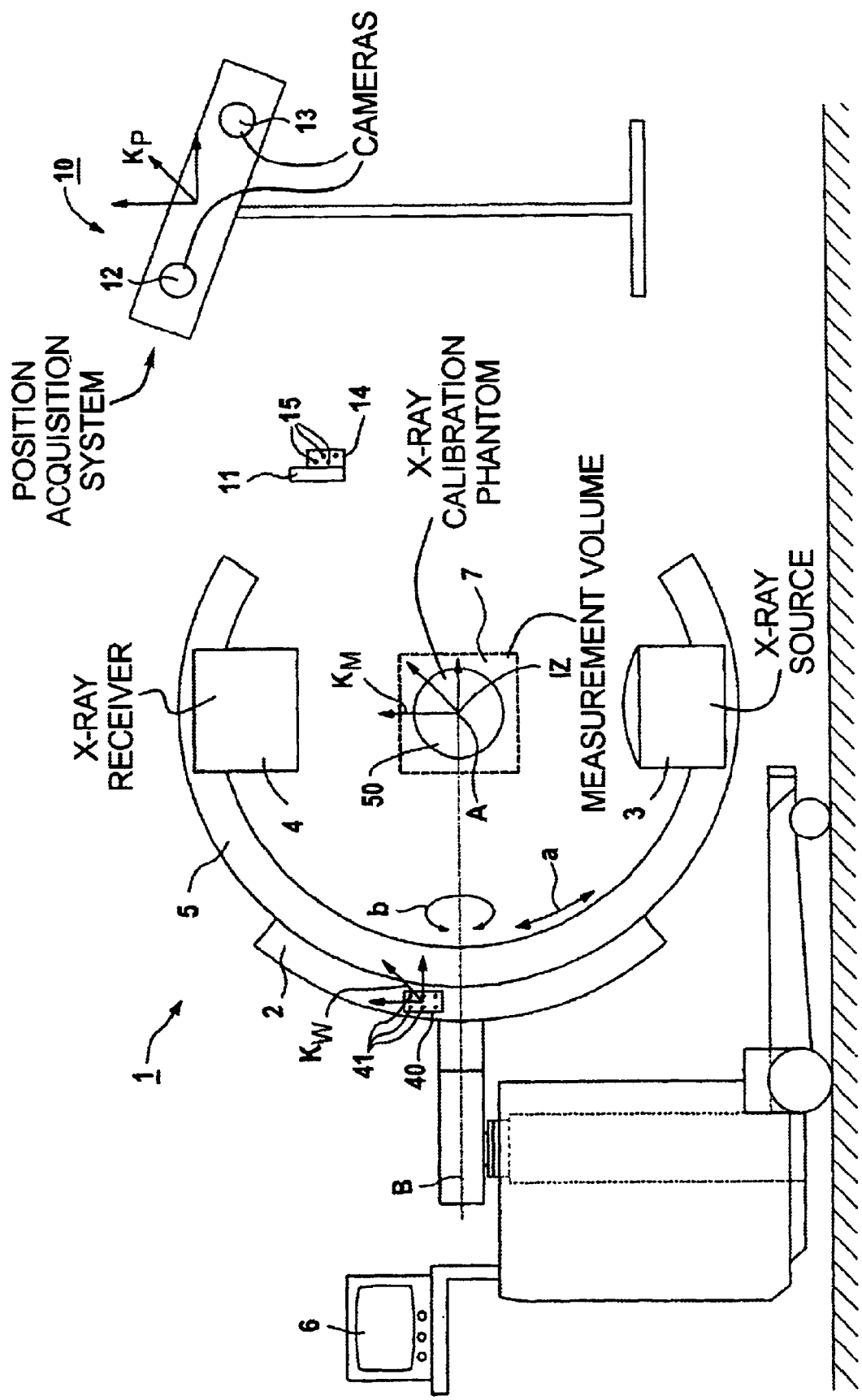
FIG. 2 is a schematic illustration of a medical interventional apparatus operable in accordance with a second embodiment of the inventive method.

Calculating means of the position acquisition system 10, for example a commercially available computer, required for identifying the position are implemented in a known way and are therefore not shown in FIGS. 1 and 2 and need not explicitly described.

Figure 3:
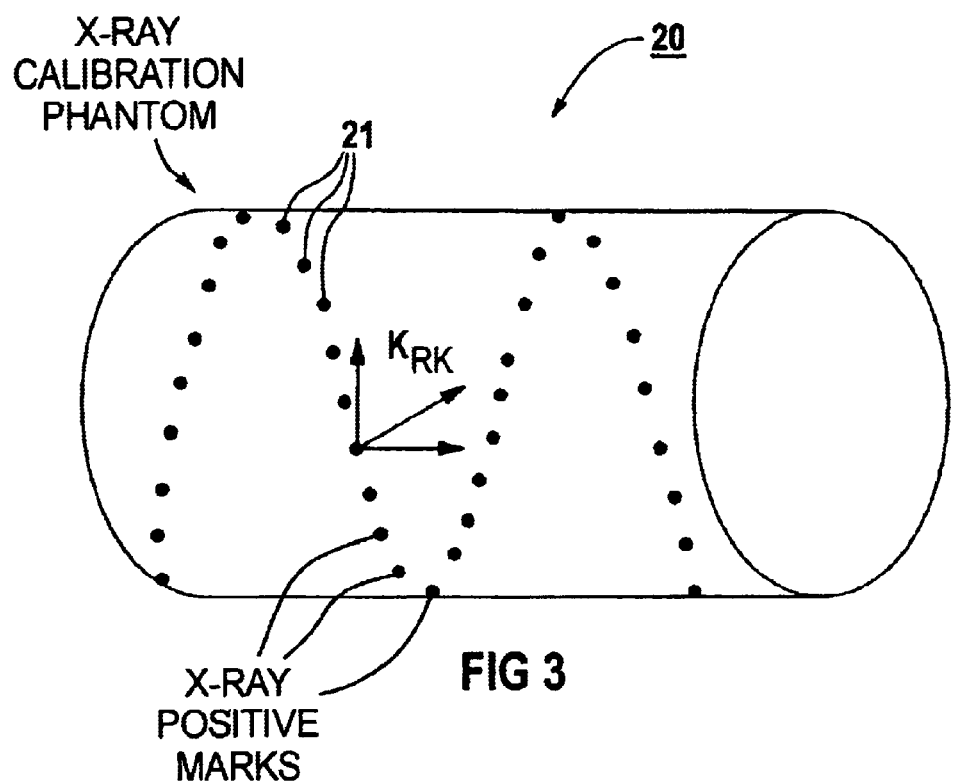
FIG. 3 shows the X-ray calibration phantom used in the embodiment of FIG. 1.

For determining the coordinate transformation, an X-ray calibration phantom 20 shown in greater detail in FIG. 3 is at least partly arranged within the measurement volume 7 of the C-arm X-ray device 1, so that the X-ray calibration phantom 20 is penetrated by an X-ray beam that emanates from the X-ray source 3 and proceeds to the X-ray receiver 4. As can be seen from FIG. 3, the X-ray calibration phantom 20 employed in the exemplary embodiment has a cylindrical shape and helically arranged X-ray-positive marks 21. In the exemplary embodiment, a series of 2D projections of the X-ray calibration phantom 20 are acquired from different projection directions upon adjustment of the C-arm 5 around its orbital axis A. The C-arm 5 is adjusted in steps in an angular range of approximately 190°. A volume of the X-ray calibration phantom 20 wherein X-ray-positive marks 21 of the X-ray calibration phantom 20 are imaged can be constructed from the acquired 2D projections in a known way with an image computer of the C-arm X-ray device 1. Following the reconstruction of the volume of the X-ray calibration phantom 20, images of X-ray-positive marks 21 of the X-ray calibration phantom 20 are selected in a freely definable sequence in the reconstructed volume, and the coordinates of the centers of gravity of the selected images in a coordinate system (not shown) allocated to the reconstructed volume are determined with a known computer program. By producing a relationship between the X-ray-positive marks 21 that are present in the measurement volume 7 and their images in the reconstructed volume, a transformation rule between the coordinate system of the reconstructed volume and the measurement volume of the C-arm X-ray device 1 can be determined, so that the coordinates of the centers of gravity of the selected marks 21 of the X-ray calibration phantom 20 that are present in the measurement volume 7 and imaged in the reconstructed volume also can be determined in the coordinate system $K_M$ allocated to the measurement volume 7. The determination of this transformation rule generally ensues in a separate calibration process with the X-ray calibration phantom 20 in which the projection matrices of the X-ray device 1 are defined for the imaging. Knowledge of the projection matrices, moreover, is required in order to be able to reconstruct a volume dataset at all from the series of 2D projections.

A navigation pointer 30 is employed for determining the coordinates of the selected X-ray-positive marks 21 of the X-ray calibration phantom 20 in the coordinate system $K_P$ allocated to the position acquisition system 10, said navigation pointer 30 being provided with optical markers 31 that can be acquired by the cameras 12, 13 of the position acquisition system 10. The optical markers 31 are arranged in a defined way at the navigation pointer 30 so that—by acquiring these markers 31—the coordinates of the tip 32 of the navigation pointer 30 in the coordinate system $K_P$ allocated to the position acquisition system 10 can be determined by the position acquisition system 10. Using the navigation pointer 30, the selected X-ray-positive marks 21 of the X-ray calibration phantom 20 that are also imaged in the reconstructed volume are tapped with the tip 32 of the navigation pointer 30 in a defined sequence. Whenever the tip 32 of the navigation pointer 30 is at one of the selected X-ray-positive marks 21, the position acquisition system 10 determines the coordinates of the tip 32 of the navigation pointer 30, and thus of the tapped mark 21 of the X-ray calibration phantom 20, in the coordinate system $K_P$ allocated to the position acquisition system 10. The X-ray-positive marks 21 each can be provided with a conical bore, so that the tip 32 of the navigation pointer 30 can be placed nearly exactly in the center of gravity of each mark 21. After the determination of the coordinates of the selected marks 21 of the X-ray calibration phantom 20 in the coordinate system $K_P$ allocated to the position acquisition system 10 in the defined sequence, accordingly, the coordinates in the coordinate system $K_M$ allocated to the measurement volume 7 as well as in the coordinate system $K_P$ allocated to the position acquisition system 10 are known for a number of X-ray-positive marks 21 of the X-ray calibration phantom 20. On th pairs, the coordinate transformation between the coordinate system $K_P$ allocated to the position acquisition system 10 and the coordinate system $K_M$ allocated to the measurement volume 7 can be determined with the image computer of the C-arm X-ray device 1 or with the computer of the position acquisition system 10 or with any other computer supplied with the corresponding information. In the exemplary embodiment, the determination of the transformation rules ensues according to an error minimization method, namely according to the method of the smallest error squares (least squares method). The transformation rule between the coordinate system $K_M$ allocated to the measurement volume 7 and the coordinate system $K_P$ allocated to the position acquisition system 10 thus has been. determined and, accordingly, is known.

In the course of a navigation-guided intervention, the cameras 12, 13 of the position acquisition system 10 acquire camera images of the instrument 11 provided. in a defined way with a marker plate 14 having optical markers 15. The positions of the instrument 11 with respect to the coordinate system $K_P$ allocated to the position acquisition system 10 thus can be determined on the basis of the camera images acquired from the marker plate 14, and these can be transformed into coordinates of the coordinate system $K_M$ of the measurement volume on the basis of the identified coordinate transformation between the coordinate system $K_P$ allocated to the position acquisition system 10 and the coordinate system $K_M$ allocated to the measurement volume 7. The positions of the instrument 11 finally, are transformed into coordinates of a reconstructed volume since the mapping of a point of the measurement volume 7 into a reconstructed volume—as already mentioned—was previously determined and thus is known. Given corresponding guidance of the instrument 11 relative to a patient, there is thus the possibility of mixing images of the instrument 11 into X-ray images of the patient made with the C-arm X-ray device 1.

In order to again be able to produce a transformation rule between the coordinate system $K_M$ allocated to the measurement volume 7 and the coordinate system $K_P$ allocated to the position acquisition system 10 after an adjustment of the C-arm X-ray device 1 and the position acquisition system 10 relative to one another, (after which the identified transformation rule would no longer be valid), a marker plate 40 with optical markers 41 that can be acquired by the cameras 12, 13 of the position acquisition system 10 is arranged at the support 2 of the C-arm X-ray device 1. The marker plate 40 has a coordinate system $K_W$ allocated to it wherein the coordinates of the optical markers 41 are known. Using the marker plate 40 and the position acquisition system 10, a coordinate transformation can be determined between the coordinate system $K_W$ allocated to the marker plate 40 and the coordinate system $K_M$ allocated to the measurement volume 7, since the coordinates of the optical markers in the coordinate system allocated to the position acquisition system 10 can be determined by the position acquisition system 10, and the coordinates of the X-ray-positive marks 21 in the coordinate system allocated to the position acquisition system 10 are known. Based on this coordinate transformation, a transformation rule between the coordinate system $K_M$ allocated to the measurement volume 7 and the coordinate system $K_P$ allocated to the position acquisition system 10 can again be determined after an adjustment of the C-arm X-ray device 1 and the position acquisition system 10 relative to one another.

In another embodiment of the invention, the determination of the coordinates of X-ray-positive marks 21 of the X-ray calibration phantom 20 in the measurement volume 7 of the C-arm X-ray device 1 ensues in a way deviating from the procedure set forth above. In this embodiment, it is thereby assumed that the geometry of the X-ray calibration phantom 20 and the coordinates of the marks 21 of the X-ray calibration phantom 20 in a coordinate system $K_{RK}$ allocated to the X-ray calibration phantom 20 are known. For determining the coordinates of the marks 21 of the X-ray calibration phantom 20 that are present in the measurement volume 7, the orientation of the X-ray calibration phantom 20 in the coordinate system $K_M$ allocated to the measurement volume is determined after the reconstruction of the volume of the X-ray calibration phantom 20. This can ensue, for example, by determining the lay of the edges of the X-ray calibration phantom 20 in a coordinate system (not shown) allocated to the reconstructed volume by means of a 3D edge extraction. As a result of the transformation rule between the coordinate system $K_M$ of the measurement volume and the coordinate system of the reconstructed volume, which is either known or can be determined based on a reconstruction of the X-ray calibration phantom 20, the orientation of the edges of the X-ray calibration phantom 20 in the coordinate system $K_M$ allocated to the measurement volume 7 also can be identified. After the determination of the orientation of the edges of the X-ray calibration phantom 20, the coordinates of the marks 21 of the X-ray calibration phantom 20 that are present in the measurement volume 7 are determined in a second step, based on the identified orientation of the X-ray calibration phantom 20 in the coordinate system $K_M$ allocated to the measurement volume 7 and based on the known coordinates of the marks 21 in the coordinate system $K_{RK}$ allocated to the X-ray calibration phantom 20. The rest of the procedure for determining the coordinate transformation corresponds to that described above, i.e., following a selection of specific X-ray-positive marks 21 in a defined sequence, the coordinates of the selected marks 21 in the sequence are determined with respect to the coordinate system $K_P$ allocated to the position acquisition system 10. Following formation of the point pairs, the transformation rule between the coordinate system $K_M$ allocated to the measurement volume 7 and the coordinate system $K_P$ allocated to the position acquisition system 10 is determined by the method of least squares.

FIG. 2 shows a second arrangement for determining a coordinate transformation for the navigation, wherein components that are structurally and functionally identical to those of the arrangement shown in FIG. 1 are provided with the same reference characters.

Figure 4:
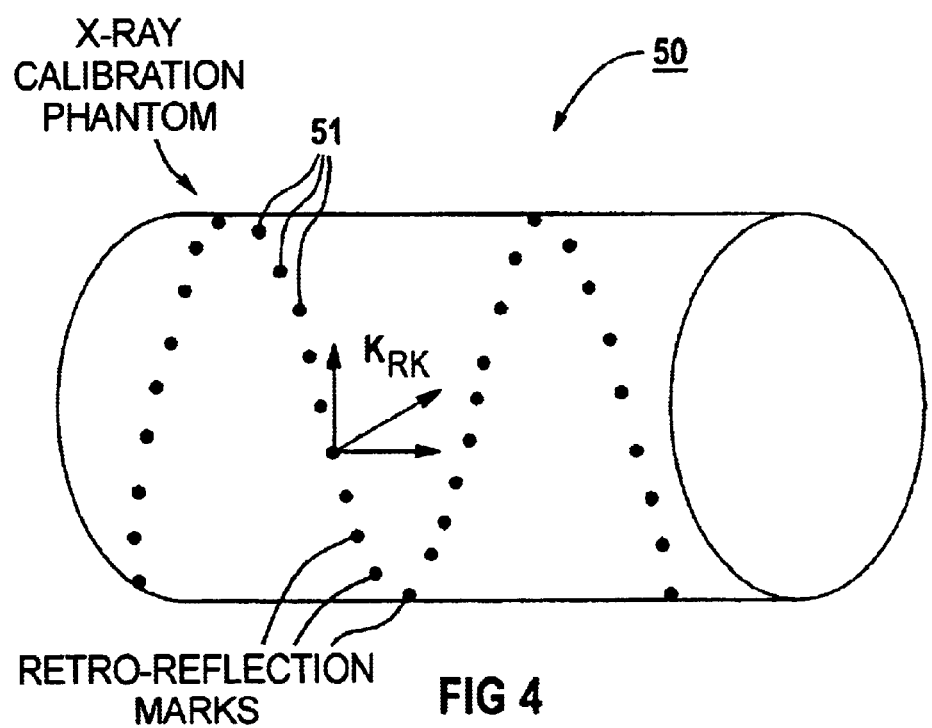
FIG. 4 shows the X-ray calibration phantom used in the embodiment of FIG. 2.

In the arrangement shown in FIG. 2, a modified X-ray calibration phantom 50 shown in FIG. 4, that likewise has X-ray-positive marks 51 is employed instead of the X-ray calibration phantom 20, whereby the X-ray-positive marks 51 are fashioned such that these also can be acquired by the, position acquisition system 10. In the exemplary embodiment, the marks 51 are of a type referred to as retro-reflection marks that can also be acquired by the cameras 12, 13 of the position acquisition system 10, as well as being X-ray positive.

As a result of fashioning the marks 51 as retro-reflection marks, the employment of a navigation pointer can be foregone for determining the coordinates of the marks 51 in the coordinate system $K_P$ allocated to the position acquisition system 10. Due to the acquisition of the marks 51 by means of the position acquisition system 10, the coordinates of the marks 51 are automatically determined by the position acquisition system 10 in the coordinate system $K_P$ allocated to the position acquisition system 10. The arrangement of the marks 51 in the X-ray calibration phantom 50 is preferably exactly known, so that point pairs can be formed in a simple way, i.e. the coordinates of a selected mark 51 in the coordinate system $K_M$ allocated to the measurement volume 7 and the coordinate system $K_P$ allocated to the position acquisition system 10 can be unambiguously allocated to said selected mark. This can be most simply achieved by the marks 21 having different sizes. After the formation of the point pairs, as already described above, the coordinate transformation between the coordinate system $K_P$ allocated to the position acquisition system 10 and the coordinate system $K_M$ allocated to the measurement volume can be determined with the method of least squares.

For determining a relationship between a point of the C-arm X-ray device 1 and the measurement volume 7 of the C-arm X-ray device 1, a marker plate 40 is again arranged at the support 2, so that a transformation rule between the coordinate system $K_W$ allocated to the marker plate 40 and the coordinate system $K_M$ allocated to the measurement volume 7 can be determined by the position acquisition system 10 in order—following an adjustment of the C-arm X-ray device 1 and the position acquisition system 10 relative to one another—to be able to determine a transformation relationship between the coordinate system $K_P$ allocated to the position acquisition system 10 and the coordinate system $K_M$ allocated to the measurement volume.

An optical position acquisition system 19 is described for the navigation in the above exemplary embodiments. Instead of the optical position acquisition system 19, however, an electromagnetic position acquisition system or a position acquisition system operating on the basis of acoustic waves alternatively can be employed. In this case, the optical markers are replaced by corresponding electromagnetic or acoustic transmission devices and the cameras are replaced by corresponding electromagnetic or acoustic reception devices.

Further, X-ray calibration phantoms other than those described can be employed for the implementation of the invention.

Moreover, the X-ray device need not necessarily be a C-arm X-ray device. For example, an X-ray device having a U-shaped carrier for the X-ray source and the X-ray receiver alternatively can be employed.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A registration method for a navigation-guided medical intervention comprising the steps of:
   using an X-ray imaging device, acquiring 2D projections of an X-ray calibration phantom, having X-ray positive marks, from different projection directions;
   reconstructing a volume of said X-ray calibration phantom from said 2D projections;
   determining respective coordinates of said X-ray positive marks, that are present in a measurement volume of said X-ray device and which are imaged in said reconstructed volume, in a coordinate system allocated to said measurement volume;
   determining coordinates of said X-ray positive marks that are present in said measurement volume and which are imaged in said reconstructed volume in a coordinate system allocated to a position acquisition system; and
   determining a coordinate transformation between said coordinate system allocated to said measurement volume and said coordinate system allocated to said position acquisition system from said coordinates of said X-ray positive marks in said coordinate system allocated to said measurement volume and said coordinates of said X-ray positive marks in said coordinate system allocated to said position acquisition system.

2. A method as claimed in claim 1 comprising selecting said X-ray positive marks that are present in said measurement volume and which are imaged in said reconstruction volume, as selected X-ray positive marks, and automatically determining the coordinates of said selected X-ray positive marks in said coordinate system allocated to said measurement volume.

3. A method as claimed in claim 1 wherein a geometry of said X-ray calibration phantom is known and wherein the coordinates of said X-ray positive marks in a coordinate system allocated to said X-ray calibration phantom is known, and wherein said method comprises, after reconstructing said volume of said X-ray calibration phantom, determining an orientation of said X-ray calibration phantom in said coordinate system allocated to said measurement volume, and determining coordinates of said X-ray positive marks, that are present in said measurement volume, in the coordinate system allocated to the measurement volume from said orientation of said X-ray calibration phantom in said coordinate system allocated to the measurement volume and from said known coordinates of the X-ray positive marks in said coordinate system allocated to the X-ray calibration phantom.

4. A method as claimed in claim 1 wherein the step of determining the coordinates of said X-ray positive marks that are present in said measurement volume and imaged in said reconstruction volume in a coordinate system allocated said position acquisitions system comprises successively designating the respective X-ray positive marks with a pointer which is identifiable by said position acquisition system.

5. A method as claimed in claim 1 comprising employing X-ray positive marks that also are acquirable by said position acquisition system.

6. A method as claimed in claim 5 comprising employing an optical position acquisition system as said position acquisition system, and employing retroreflection marks as said X-ray positive marks.

7. A method as claimed in claim 5 comprising, in said position acquisition system, automatically determining the coordinates of the X-ray positive marks in said coordinate system allocated to said position acquisition system.

8. A method as claimed in claim 1 comprising determining said coordinate transformation between said coordinate system allocated to the measurement volume and said coordinate system allocated to the position acquisition system using a method of least squares.

9. A method as claimed in claim 1 comprising disposing markers detectable by said position acquisition system at said X-ray imaging device.

10. A method as claimed in claim 9 comprising determining a coordinate transformation between a coordinate system allocated to said markers arranged at said X-ray device and said coordinate system allocated to the measurement volume, from respective positions of said markers detected by said position acquisition system.

11. A method as claimed in claim 1 comprising employing a C-arm X-ray device as said X-ray imaging device.

* * * * *